US010283014B2

United States Patent
Baker et al.

(10) Patent No.: US 10,283,014 B2
(45) Date of Patent: May 7, 2019

(54) SMART PACKAGING AND DISPLAY SYSTEM

(71) Applicants: Jeff Baker, Orlando, FL (US); Paul van der Pol, Winter Garden, FL (US); Craig Baker, Lebanon, OH (US); Mark Bunker, Orlando, FL (US); Seth Freytag, Winter Springs, FL (US); Karina Marulanda, Orlando, FL (US); Michael Siemer, Orlando, FL (US); Matthew Palyo, Orlando, FL (US)

(72) Inventors: Jeff Baker, Orlando, FL (US); Paul van der Pol, Winter Garden, FL (US); Craig Baker, Lebanon, OH (US); Mark Bunker, Orlando, FL (US); Seth Freytag, Winter Springs, FL (US); Karina Marulanda, Orlando, FL (US); Michael Siemer, Orlando, FL (US); Matthew Palyo, Orlando, FL (US)

(73) Assignee: JBCB HOLDINGS, LLC, Orlando, FL (US)

( * ) Notice: Subject to any disclaimer, the term of this patent is extended or adjusted under 35 U.S.C. 154(b) by 125 days.

(21) Appl. No.: 14/293,534

(22) Filed: Jun. 2, 2014

(65) Prior Publication Data
US 2015/0004582 A1 Jan. 1, 2015

Related U.S. Application Data

(63) Continuation-in-part of application No. 13/650,676, filed on Oct. 12, 2012.
(Continued)

(51) Int. Cl.
*G09B 23/28* (2006.01)
*G09B 19/00* (2006.01)

(52) U.S. Cl.
CPC .......... *G09B 23/285* (2013.01); *G09B 19/00* (2013.01)

(58) Field of Classification Search
CPC .. G06F 19/3468; G06F 19/34; G06F 19/3462; A61M 5/24; A61M 5/31525; G09B 23/285; G09B 9/00
See application file for complete search history.

(56) References Cited

U.S. PATENT DOCUMENTS 5,328,460 A 7/1994 Peter et al.
6,997,906 B2 * 2/2006 Langley ............ A61M 5/14244
128/DIG. 1
(Continued)

FOREIGN PATENT DOCUMENTS

WO 1990010470 A1 9/1990
WO 2011117212 9/2011
(Continued)

*Primary Examiner* — Jerry-Daryl Fletcher
(74) *Attorney, Agent, or Firm* — Timothy H. Van Dyke; Beusse, Wolter, Sanks & Maire PLLC

(57) ABSTRACT

An embodiment of a medicament training system configured to provide instructions for using a medicament device to a user in a sequence of steps is provided. The medicament training system includes including a medicament training container, a medicament device, wherein the medicament training container communicatingly connects to the medicament device, a signal output component associated with the medicament training container, and circuitry associated with the medicament training container configured so as to control a provision of the instructions to the user in the sequence of steps.

26 Claims, 12 Drawing Sheets

Related U.S. Application Data

(60) Provisional application No. 61/620,168, filed on Apr. 4, 2012.

(56) References Cited

U.S. PATENT DOCUMENTS

| | | |
|---|---|---|
| 7,713,229 B2 | 5/2010 | Veti et al. |
| 8,172,082 B2 * | 5/2012 | Edwards ............... A61M 5/19 206/363 |
| 8,361,026 B2 | 1/2013 | Edwards et al. |
| 8,551,039 B2 | 10/2013 | Veit et al. |
| 8,690,827 B2 | 4/2014 | Edwards et al. |
| 9,022,980 B2 | 5/2015 | Edwards et al. |
| 9,101,723 B2 | 8/2015 | Larsen |
| 9,125,991 B2 | 9/2015 | Schabbach et al. |
| 9,233,210 B2 | 1/2016 | Bock et al. |
| 2005/0182358 A1 | 8/2005 | Veit et al. |
| 2006/0135907 A1 | 6/2006 | Remde et al. |
| 2008/0188813 A1 | 8/2008 | Miller et al. |
| 2012/0293321 A1 | 11/2012 | Monroe |
| 2013/0151162 A1 | 6/2013 | Harris et al. |
| 2014/0207080 A1 | 7/2014 | Allerdings et al. |
| 2014/0243749 A1 | 8/2014 | Edwards et al. |
| 2015/0018770 A1 | 1/2015 | Baran et al. |
| 2015/0032059 A1 | 1/2015 | Allerdings et al. |
| 2015/0290396 A1 | 10/2015 | Nagar et al. |
| 2015/0306304 A1 | 10/2015 | Schabbach et al. |
| 2016/0129182 A1 | 5/2016 | Schuster et al. |
| 2016/0166766 A1 | 6/2016 | Schuster et al. |

FOREIGN PATENT DOCUMENTS

| | | |
|---|---|---|
| WO | 2013120775 | 8/2013 |
| WO | 2013120776 | 8/2013 |
| WO | 2013120777 | 8/2013 |
| WO | 2015052519 | 4/2015 |

* cited by examiner

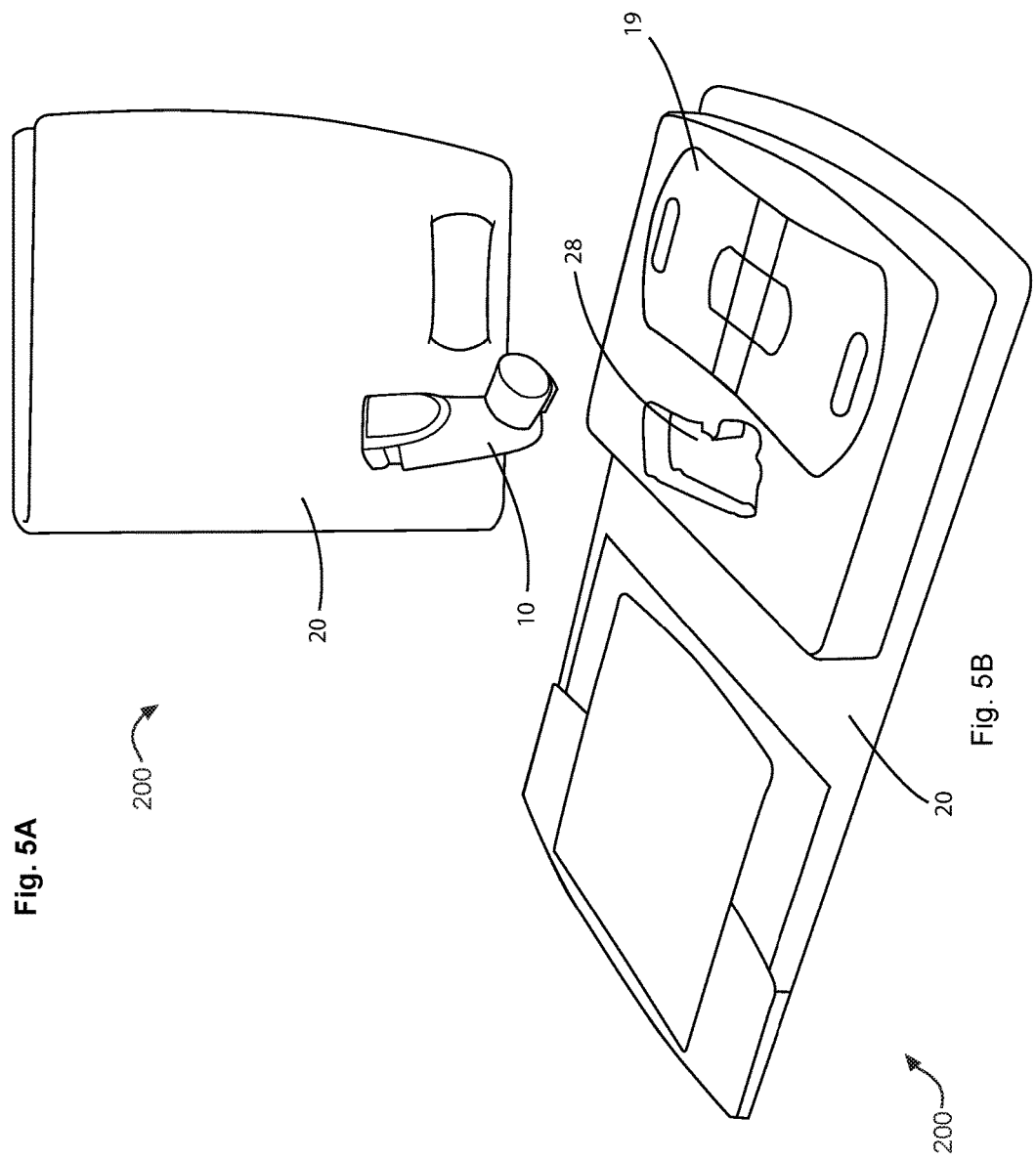

SMART PACKAGING AND DISPLAY SYSTEM

CROSS REFERENCE TO RELATED APPLICATIONS

This application is related to U.S. Provisional Application No. 61/620,168 filed on Apr. 4, 2012, and U.S. Non-Provisional application Ser. No. 13/650,676 filed Oct. 12, 2012 to which priority is claimed in accordance with 35 USC 119 and 35 USC 120, respectively. The entirety of each of these applications is incorporated by reference herein.

FIELD OF INVENTION

Exemplary embodiments of the present disclosure relate to training and display devices for interfacing with a medicament training device, wherein a user can be trained to use the device with the assistance of the display and/or package in some embodiments. Embodiments disclosed herein may include training devices and packaging and/or displays having associated circuitry configurable or programmable to guide a user through the training for using the actual medicament device.

BACKGROUND

Performing a medical treatment or test on oneself carries with it certain risks and often creates a level of anxiety for the user performing the treatment or test. It has proven beneficial in the medical field to practice various medical techniques including drug delivery, specifically where it relates to injections and other invasive drug delivery means prior to delivering the medications to a patient in need, and particularly in the case of self-administration of medicaments. Training devices are helpful in reducing errors and anxiety associated with self administering medical treatment, as well as increasing efficiency and accuracy in providing the treatment to patients. Medical devices can be intimidating to use; the fear associated with giving oneself an injection, for example, can be traumatic. This fear is increased in persons with little or no experience in self-administration of medications. Consequently, devices and methods to assist in training individuals to inject themselves or otherwise self-administer medication are beneficial in decreasing or preventing the anxiety associated with medicament delivery. Medicament delivery training devices allow patients to practice giving themselves a full dose in a safe and effective manner.

SUMMARY

An embodiment of a medicament training system configured to provide instructions for using a medicament device to a user in a sequence of steps is provided. The medicament training system includes including a medicament training container, a medicament device, wherein the medicament training container communicatingly connects to the medicament device, a signal output component associated with the medicament training container, and circuitry associated with the medicament training container configured so as to control a provision of the instructions to the user in the sequence of steps.

Another embodiment of a medicament training system configured to provide instructions for using a medicament device to a user in a sequence of steps is provided. The system includes a medicament training container, a medicament device, wherein the medicament training container communicatingly connects to the medicament device, a signal output component associated with the medicament training container to provide the sequence of steps and/or feedback to the user, wherein the output from the signal output component is at least one of visual, auditory, tactile, olfactory, or gustatory. The medicament training system further includes circuitry associated with the medicament training container configured so as to control a provision of the instructions to the user in the sequence of steps, one or more sensors associated with the medicament training container and/or the medicament device, a microprocessor associated with the circuitry and the one or more sensors, a memory module configured to store the instructions, and a control interface associated with the medicament training container and/or the medicament device, said control interface comprising one or more responsive members reactive to user input.

In a further embodiment, a medicament training system configured to provide instructions for using the system to a user in a sequence of steps is provided. The medicament training system includes a medicament training container, a medicament device, one or more sensors, a microprocessor, one or more signal output components for providing an output to the user. The medicament training system embodiment includes a storage medium component associated with the microprocessor comprising a database of instructions pertaining to the sequence of steps for using the system stored thereon, one or more program code modules stored on the microprocessor or the storage medium component wherein the one or more program code modules comprise a first program code module for causing the microprocessor to provide a first instruction of the sequence of steps; and a second program code module for causing the microprocessor to provide a subsequent instruction based on a current register.

BRIEF DESCRIPTION OF THE DRAWINGS

FIG. 5A provides a front view of an embodiment of the system.

FIG. 5B provides a perspective view of the embodiment of FIG. 5A in an open position.

DETAILED DESCRIPTION

Figure 1A:
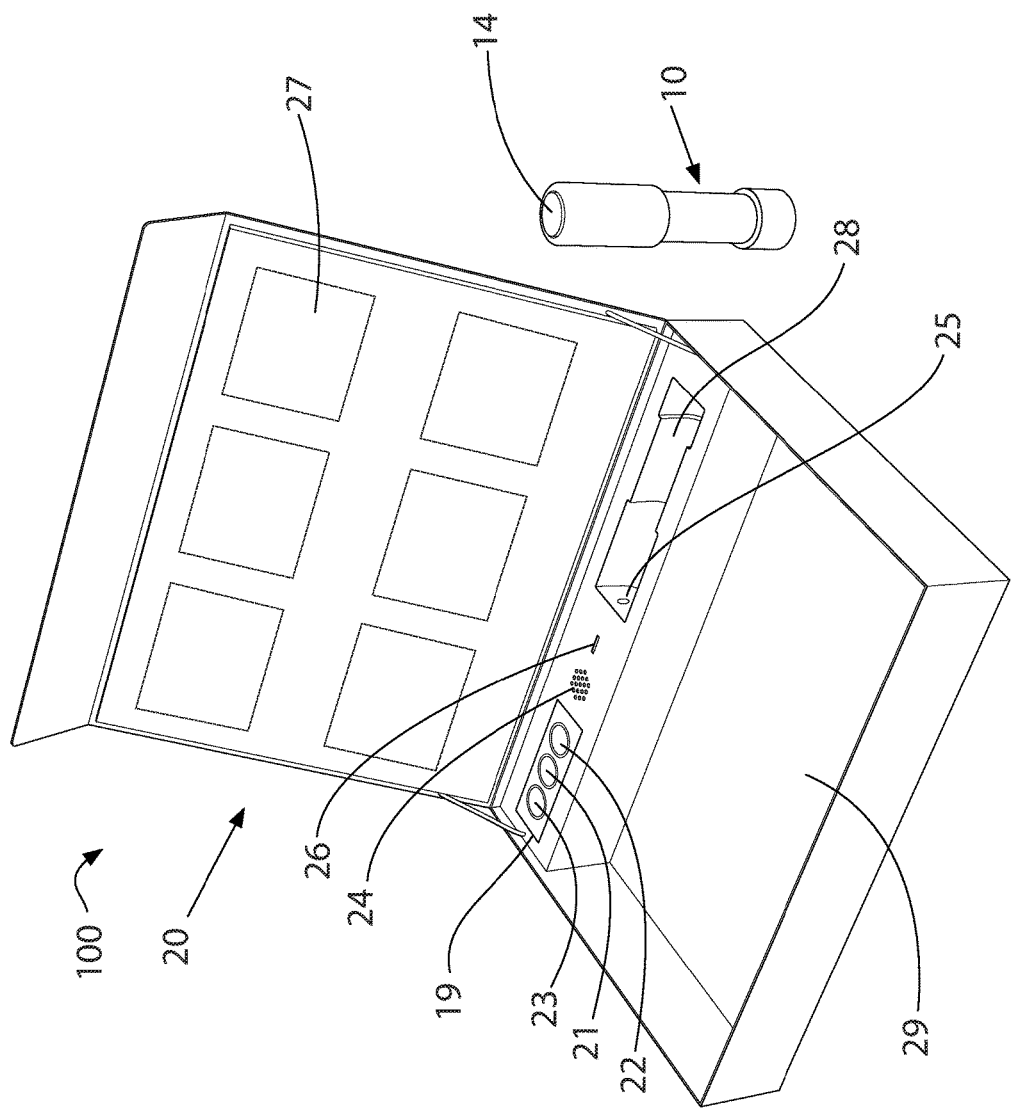
FIG. 1A provides a perspective view of an embodiment of the system.

For the purposes of promoting an understanding of the principles and operation of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to those skilled in the art to which the invention pertains.

The inventors have identified a need for a system to assist users in administering medication or training for medication administration. Various modes of administration are provided by the system embodiments disclosed herein including parenterally administered medications, inhaler-based medications, among other modes of administration. Embodiments of the system described in greater detail below include applications for home use, in-office use by health care provider (HCP) or by the patient, hospital use, and educational use for training medical professionals and other personnel among other potential uses. The inventors have discovered a system for training individuals to use medical devices while improving user comfort and confidence in delivery and administration of medicament.

In addition to increasing confidence in self-administration in users by practicing with a medicament training system, the inventors have identified additional benefits associated with multi-sensory learning regarding a medicament training system. It has been discovered that multi-sensory learning establishes multiple pathways in separate areas in the brain and ultimately results in a highly effective learning experience. However, in order to gain benefits from multi-sensory learning devices, certain requirements must be met including but not limited to the following: the sources of stimuli must be in close proximity to one another; the sources of stimuli must be synchronous; the stimuli must be congruous semantically, otherwise the superior colliculus (area of the brain located in the midbrain known for integrating multiple sources of information) will segregate the stimuli instead of integrate them; and finally, the use of extraneous materials must be limited. With knowledge of the essential factors in multi-sensory learning and incorporation of the multi-sensory learning features into a training system, the inventors have developed a novel, cutting-edge medicament training system.

Exemplary embodiments of the medicament delivery training device can be implemented to educate users on the proper operation and usage of a medicament device. The medicament training system can be used to make prospective and current users of medicament devices feel more comfortable and confident in self-administration (or administration to others) of medicaments, and can help users understand the proper steps of medicament delivery.

Exemplary embodiments of the medicament training system can be used by a user before the user administers a medication by way of, for example, an auto-injector by way of using an actual automatic injection device corresponding to the automatic injection training device and/or can be used as needed or desired by the user. Other exemplary embodiments of the invention herein pertain to manual injection devices and manual injection training devices used by the user, respiratory inhaler trainers and respiratory inhaler drug delivery devices, in non-limiting examples.

The medicament training system takes advantage of the multisensory learning capabilities of the human brain. As such, the medicament training system provides the means to stimulate primarily the visual, auditory and somatic systems of the human nervous system.

Visual stimuli or feedback (visual output) can be generated mechanically or electronically. An example of a mechanically generated visual stimulus is a plunger moving past an inspection window in an autoinjector or prefilled syringe medicament device or a shroud extending from an injection device. An example of an electronically generated visual stimulus is one or more LED's blinking, an LCD display showing an icon, or key steps in the process of administration being highlighted on a screen in the order required for proper administration of medicament, in non-limiting examples. A visual output as disclosed herein includes but is not limited to a light, a display, a colorometric display system, a change in position of the device or any other type of visual cue to the user of the container and/or device. The visual output is associated with the medicament device or with the medicament training container; therefore it may be disposed on either portion of the system or provided in connection with the system either by a wire or wirelessly.

Additional visual outputs that may be incorporated into the system herein may include display devices having one or more layers of material having a light transmission region, a unit of information to be highlighted, and a light blocking region; and a backlight unit having a flexible, planar waveguide body, a light source configured to direct light into the waveguide body, and at least one light director associated with a portion of the waveguide body so as to direct light transversely to a plane of the waveguide body. The directed light travels through the light transmission region, and the directed light is directed toward the unit of information to be highlighted as provided in International Application No. PCT/US11/26976 and U.S. National Stage application Ser. No. 13/582,560 which claim the benefit of U.S. Provisional Application Ser. No. 61/310,081, which are incorporated by reference in their entireties herein. The unit or units of information to be highlighted may include the stepwise instructions for administering the medicament to a user and may also provide the duration of each step by way of highlighting each step for a predetermined amount of time such that the user can follow the precise timing of each step in the sequence.

Auditory stimuli or feedback (audio output) can also be generated mechanically or electronically. An example of a mechanically generated auditory stimulus is the "click" that can be heard if two parts of a device interlock. An example of an electronically generated auditory stimulus is a beeper or a speaker that plays spoken instructions. An audio output as disclosed herein includes but is not limited to music, a sound, a beep, a series of beeps music or sounds, a mechanical sound including clicking, a sound replication of operation or behavior of a drug delivery device containing medicament. These auditory stimuli, such as two parts of a device interlocking can be picked up by a microphone of the system. The system can then identify whether or not the device was used correctly (i.e., whether a step was performed correctly or in the correct order, for example). A combination of both visual and auditory output may include a video tutorial providing instructions to a user on proper administration of the medicament or use of the training device, for example.

Somatic stimuli or feedback, also called somatosensory stimuli or tactile feedback, is typically generated mechanically. In a typical embodiment of the medicament training system, there are a large number of somatic stimuli, particularly with reference to the medicament device, such as actuation forces, abrasion resistance, frictional forces, spring compression, the feel of a click if two parts interlocking, surface texture, vibrations, weight sensation, and any other similar stimuli or feedback known to those of skill in the art.

A "predetermined value" as used herein, for example, includes but is not limited to a value or range of values relating to an event involving use or operation of the device. These may include, but are not limited to thresholds, ceilings, baselines or range values that are desired or undesired for a particular event. Examples of predetermined values include, but are not limited to, a predetermined orientation value, predetermined time value, or a predetermined contact value, in addition to other predetermined values described herein refers to a value that is used as a reference value in relation to a value, signal, or indication that is detected by, for example, a sensor of the medicament device. Predetermined value may include an optimal value, or a sub-optimal value, or any value there between, or any combination thereof. The term "value" as used herein, may refer to a specific value or a range of values.

In one example, a predetermined perpendicularity value may include a 90 degree angle between the device and a target region for the medicament device, an additional predetermined perpendicularity value may include a 10 degree angle between the device and a target region for the device. At either predetermined perpendicularity value, or at any value there between, a signal output component may be initiated. The signal output component may therefore be an error message or a congratulatory message, for example. This signal output component may be initiated from the medicament device and/or the medicament training container.

The term "condition" as used herein includes but is not limited to one or a combination of a user input, a status of the medicament device or the medicament training container, anything that is sensed by the device or container, correct or incorrect stepwise activities, usage of the device over time, among other conditions.

The term "error condition" as used herein includes but is not limited to one or a combination of a condition pertaining to a mistake by the user in using the device, whether the mistake is incorrect positioning or contact between the device and the user, or whether the mistake is an out of order step, a step that exceeds or fails to meet predetermined time value (such as an undue pause during or between steps, or insufficient time for conducting a step or transition between steps). Error conditions may also include errors of the device itself or of the container, including low or lack of power or failure to operate as intended.

The term reconstituted as used herein includes a return of the components to their original state. For example, following use of the medicament device, once the device is in a post-delivery state (or post training state), it can be reset for subsequent use. As part of the resetting of the device from a post-delivery (or post-training) state to a pre-delivery (or pre-training) state, the signal output components including audio, visual, olfactory, gustatory, and tactile are also reset back to their original states, or reconstituted, such that a subsequent training or medicament delivery can be performed with the device. The term reconstituted may also include return of the medicament training container to its original state and may include a return of the stepwise instructions to the first step in the sequence or a replacement of the medicament device within the medicament training container in preparation for a subsequent medicament delivery or training, for example.

The term "medicament training container" or "container" as discussed herein may include a display, a package, or a housing for retaining or connecting to and/or associating with at least a portion of the medicament device. The display or housing may be configured to provide one or more outputs to a user during use of the system, or be configured to receive inputs from a user via a control interface associated therewith, in non-limiting examples. The medicament training container may include a power source (i.e., battery) for the system, and the device may be entirely passive in one embodiment. In other embodiments, as will be described in more detail below, no power source is necessary for operation of the system. The medicament training container may also include a speaker, in one embodiment. Inclusion of a speaker and/or power source in the container allows the speaker and the power source to be larger than they would ordinarily be if included in the medicament device.

The term "associated" or "association," as used herein, includes but is not limited to direct and indirect attachment, adjacent to, in contact with, partially or fully attached to, and/or in close proximity therewith. The term "in conjunction with" as used herein includes but is not limited to synchronously or near synchronous timing, the phrase may also include the timing of outputs, where one output directly follows another output.

Any of the abovementioned outputs by the signal output component can be presented along with or in conjunction with any of the other outputs of the device. For example, a visual and an audio stimulation or feedback may occur at the same time or within the same step of the training to enhance training of the user. Furthermore, the inventors have discovered that a combination of mechanical feedback (kinesthetic) and electronic feedback enhances the learning experience of a user when using the medicament training system.

In an embodiment, the medicament training system includes a sensor to detect a condition of the medicament device, wherein an output of the system from the signal output component is initiated in response to a predetermined value for a condition. One or more sensors may be provided on the medicament device, in an embodiment. In one particular embodiment, the sensor may be an orientation sensor provided to detect an orientation of the medicament device, wherein the signal output component is initiated if the orientation of the medicament device meets a predetermined orientation. The orientation dictates the position of the device relative to another object, for example, relative to the user during use of the system. In some instances, particular drug delivery devices must be oriented in a certain orientation for optimal drug therapy results. For example, in regard to parenteral administrations, the delivery device must be oriented such that the needle is beneath, in some instances, the body part being injected so as to avoid air bubbles in the medicament while in the device prior to its injection into the user. In other embodiments, the needle must be angled in a downward facing direction toward the target area to remove any air that may be contained within the medicament chamber or needle portion. For medications administered by way of a respiratory inhaler device, the device must be oriented in a particular manner such that the patient receives the intended dose of the medicament. Certain medications may require certain modes of delivery or application, and may dictate the orientation of the device during delivery. The orientation sensor is useful in identifying the proper orientation for the device based on the medicament being administrated or the type of delivery device.

In another embodiment, a contact sensor may be provided to detect a contact or insufficient contact between the device and the user, wherein the signal output component is initiated if the contact of the device meets a predetermined contact value, or in other instances if the contact of the device fails to meet the predetermined contact value. This predetermined contact value may be set at 100% contact between the device and the portion of the body of the user being used for the delivery of the medicament, or the contact value may be set between 90-99%, or 80-88% contact such that a user can be made aware when there is sufficient contact between the device and the user for adequate delivery of the medicament from the device. The sensor can be configured to sense the angle between a longitudinal axis of the device and the surface of the user where the delivery of the medicament is to occur. Additionally, or alternatively, in some circumstances contact sensors may be provide don the portion of the device which is intended to contact the surface of the user where delivery of the medicament is to occur, therefore the contact sensor can alert the user when sufficient contact has been made. The contact sensor can also alert the user when sufficient contact has not been made with the surface of the user.

Contact sensors may be provided on the actuation button, on a shroud of the device, on a cap or plunger of the device, for example. These contact sensors may be provided to open or close a circuit within the device to provide feedback to a user.

Additional sensors which may be integrated into or associated with the system herein includes perpendicularity sensors, air flow sensors, and accelerometers (for shaking or orientation, for example). Some of these sensors may require a supply of voltage. The medicament training container may include one or more of the sensors described herein, for example, a contact sensor may be used to detect removal or placement of the device within the medicament training container, for example. A microphone may be included to detect movement of parts of a medicament device relative to one another, such as clicks from an auto injector medicament delivery or training device, for example. The microphone may also register the sound of a respiratory training device, such as a click from two interlocking or intercommunicating parts of the device or a whistle, wherein the whistle may indicate correct or incorrect usage of the device to a user of the system.

The term "connected" as used herein includes wireless or wire connection. The external source includes a database, a remote computer, and also includes communications with another device, another container, a network, and any other means of communication or transfer of information known in the art. Connected may further refer to a direct surface to surface connection between the device and another surface or an indirect contact there between. In some embodiments, the device may communicate with a remote device either via a wired or a wireless connection. The remote device may be, for example, a remote communications network, a computer, a cell phone, a personal digital assistant (PDA) or the like. Such an arrangement can be used, for example, to download replacement processor-readable code from a central network to the memory module or other memory of the device. In some embodiments, the circuitry of the device can download or obtain information associated with a medicament drug delivery or training device or particular medicament, such as an expiration date, a recall notice, updated use instructions or the like.

The term "communicatingly connects" as used herein includes both two way communication and one way communication such as input received from the device, for example, an auditory signal or visual signal, for example, electromagnetic induction, RFID, Bluetooth connection, wireless and wired connections.

The network interface can be configured to transmit information to and/or from the circuitry of the device to and/or from a central network, such as, for example, an emergency response network. In some embodiments, for example, the device can notify an emergency responder when and how a medicament delivery training device is used. In other embodiments, the device can transmit information to and/or from a third party, such as a physician, an emergency contact and/or the manufacturer of a medicament device, when and how the medicament delivery training device is used. Such information can include, for example, the location of use, the date and/or time of use, the efficiency of use including conditions and errors of use, or the like.

An indicator as described herein can be used to indicate to a user that a particular step or that the entire simulation is complete, or that the particular step or simulation is nearing completion. The indicator can also indicate predetermined statuses including elapsed time, and insufficient time between steps, for example. There may be one or more indicators, and each indicator may provide an indication to the user that the medicament delivery simulation is complete by an audio, visual, tactile, or a smellant (olfactory) indication, taste indicator (gustatory), or a combination thereof.

Parenteral delivery devices and trainers described herein include, but are not limited to, any type of medicament device (for delivery or training and/or simulation) which provides administration of a medicament or simulation thereof via intravenous or intramuscular injection, for example, such as an autoinjector, a pre-filled syringe, IV fluid therapy including total parenteral nutrition methods (TPN), peripherally-inserted central catheter (PICC) line, or other related devices. The medicament training system embodiments herein also include but are not limited to medicament delivery devices and training devices for oral or intravenous administration by liquid, capsule, tablet, or spray. Medicament delivery devices and training devices for administration or training by injection, whether intramuscular, intravenous, intraperitoneal or by any parenteral route are also contemplated herein. Medicament delivery devices and training devices for parenteral administration by bolus injection or by continuous infusion are also contemplated herein. Medicament delivery devices and medicament training devices for administration via an inhaler or for buccal, urethral, vaginal, or rectal administration, topical administration in a cream, lotion, salve, emulsion, or other fluid are also contemplated herein.

As used herein, the term "administering" or "administration" includes but is not limited to oral or intravenous administration by liquid, capsule, tablet, or spray. Administration may be by injection, whether intramuscular, intravenous, intraperitoneal or by any parenteral route. Parenteral administration can be by bolus injection or by continuous infusion. Formulations for injection may be presented in unit dosage form, for example, in ampoules or in multi-dose containers with an added preservative. The compositions may take the form of suspensions, solutions or emulsions in oily or aqueous vehicles and may contain formulatory agents such as suspending, stabilizing and/or dispersing agents.

Alternatively the compositions may be in powder form (e.g., lyophilized) for constitution with a suitable vehicle, for example sterile pyrogen-free water, before use. Compositions may be delivered to a subject by inhalation by any presently known suitable technique including a pressurized aerosol spray, where the dosage unit may be controlled using a valve to deliver a metered amount.

Administration by capsule and cartridges containing powder mix of the composition can be used in an inhaler or insufflator to deliver the particles to the subject. Still other routes of administration which may be used include buccal, urethral, vaginal, or rectal administration, topical administration in a cream, lotion, salve, emulsion, or other fluid may also be used.

The term "medicament" as used in describing the various embodiments of this invention includes an injectable liquid medicine, medication, drug, pharmaceutical, prescriptive, agent, antidote, anti-venom, hormone, stimulant, vasodilator, anesthetic, nutritional supplement, vitamin and/or mineral compound, saline solution, biological, organic compound, genetically and/or chemically modified protein and/or nucleic acids, or other liquid that is adapted to be injected into the tissue of a subject.

Embodiments of the invention may include a printed circuit board with a simple microcontroller. The microcontroller runs the embedded software and interacts with memory. A timer may be included in the microcontroller. The microcontroller may incorporate an audio processor (see below).

Audio Processor

Audio implementation may include a digital audio processor (codec+amplifier) and a speaker. The audio technology in the package may have some or all of the following characteristics: peak volume dB (SPL) at 1 meter (3.2 feet) is at minimum 55 dB (at 850 Hz), the bit depth of the audio chip is 16-bit, the audio sampling rate is 16 kHz, maximum bit rate (hardware) is 256 kbps, available memory size for audio storage is 32 MB, in non-limiting examples.

Power Source

Embodiments of the invention may be powered by batteries, in one example. The medicament training container may include a battery, which can be larger than the battery in the medicament device. As a result of the various non-limiting examples of architectures described herein, the medicament device battery can be very small in some embodiments. Batteries in the container can be large and rechargeable and/or replaceable. Primary and secondary batteries may be included for backup. The container may be powered through a converter which plugs into an outlet. Alternatively, a charger and/or cradle can be used to charge the components of the system described herein.

A control interface may be provided on the medicament device, on the container and/or associated with the system either directly or indirectly. The control interface can be used for generating user commands, and the circuitry disposed within the device or the container or in association with the device or container is in communication with the control interface. The circuitry may be embodied as a processor-based circuit, wherein it is configured and arranged to receive input from the user via the control interface, wherein the processor-based circuit includes an audio signal processor configured and arranged to provide audio to the user to instruct the user while using the system during the training or delivery, wherein the audio may be controlled by the responsive member on the control interface via user input.

The system may include at least one responsive member that is reactive to user input. The responsive member may include a button, either virtual or non-virtual, a switch, a touch sensor, a toggle, a heat or tactilely sensitive response sensor, or any combination thereof, or any other such device as known in the art. The responsive member may be part of the control interface of the device or the container.

The control interface may provide the user with the ability to change the language of the audio output of the device. Languages in which the audio output may be communicated to a user include but are not limited to, English, Spanish, French, Arabic, Portuguese, Russian, Chinese, Vietnamese and Japanese. It is known to those of skill in the art that any language may be provided via the audio output of the device. User controls such as on/off controls, play/pause controls, previous, selected language or set volume may be controlled through the control interface. However, in some embodiments, the on/off and play/pause/stop features of the system may be controlled by simply removing and replacing the device within the container by way of a sensor that detects removal and replacement of the device within the container. Alternatively, the system may be powered on or off automatically or after a predetermined time period.

Certain embodiments of the system may have error recognition and correction capabilities, and others may include an algorithm which can track the sequence of scripts or instructions and retrieve, at a certain time, the proper script or instruction from a lookup table. Some embodiments may include audio instructions only, and others may include video instructions, table display instructions and/or a combination of any or all of the above, for example. Other embodiments of the system may include user and/or sensor inputs as interruptions to the script or instructions provided by the system.

Communication between the device and the container may be established by wireless connection, for example through a Bluetooth® transceiver. An antenna may be required and the system may require power as described above. Components of this communication type will be in both the container and the device, for example. Another method of communication includes a wire communication using a data communication bus, or device interface bus such as I²C or PCI bus, for example. Another example of communication between the container and the device used in embodiments of the system herein includes communication between an RFID transponder and an RFID reader. Either one of the transpoder and the reader can be in the device and the other component in the container. In one embodiment using the RFID technology to communicate between the components of the system, one way communication of data can occur. The RFID transponder can be powered by the RFID reader and therefore does not require a battery. In one example, the container can include the RFID reader and the device can include the RFID transponder such that the device does not require a battery.

An embodiment of a medicament training system configured to provide instructions for using a medicament device to a user in a sequence of steps is provided. The medicament training system includes including a medicament training container, a medicament device, wherein the medicament training container communicatingly connects to the medicament device, a signal output component associated with the medicament training container, and circuitry associated with the medicament training container configured so as to control a provision of the instructions to the user in the sequence. In another embodiment, at least a portion of the medicament device is housed within at least a portion of the medicament training container. In a further embodiment, when the medicament device is removed from the medicament training container, the provision of instructions is initiated. In still a further embodiment, when the medicament device is removed from the medicament training container, the system is powered on. In another embodiment, the medicament training system is provided wherein the medicament device communicatingly connects to the medicament delivery training container with a wired connection and/or a wireless connection. In a further embodiment, the wireless connection comprises Bluetooth® technology and/or Radio-Frequency Identification (RFID) technology. In a further embodiment, the medicament training system includes an attachment device. The attachment device may be configured to associate with the medicament device and/or the medicament training container by a wired or a wireless connection. In a further embodiment, the attachment device may include at least one sensor. The attachment device may include circuitry associated therewith configured so as to control a provision of a sequence of step instructions to the user. The instructions may pertain to the usage of the medicament device, and may be used to train a user to use the medicament device for a training session or to walk a user through the delivery or administration of medicament with the medicament device, or both, in non-limiting embodiments.

In one embodiment, the medicament device is a medicament training device. In a further embodiment, the medicament training device comprises at least one of a respiratory inhaler trainer and a parenteral drug delivery trainer. The medicament training device may also be configured to deliver medicament (ie., provide administration of medicament) in some embodiments. The device is not limited to either of these embodiments, however, and can also be provided for transdermal, intraoptical, intra vaginal, intra rectal, oral, nasal, and other modes of administration of medicament (i.e., medicament delivery) or training for medicament delivery as described herein. In one embodiment, the medicament device is a medicament delivery device configured for medicament delivery to a user. In addition to delivering medicament (i.e., administering medicament to a subject) the medicament delivery device may also be provided, in some embodiments, to function as a medicament training device.

In a further embodiment, the medicament delivery device includes at least one of a respiratory inhaler and a parenteral drug delivery device. The medicament delivery device and/or medicament training device may be provided for use via multiple modes of administration discussed herein.

In one embodiment, the medicament training system is provided wherein the medicament training container detects a condition of the system. In a further embodiment, the medicament training container includes a sensor to detect a condition of the medicament device. In still a further embodiment, the medicament training system is provided wherein an output from the signal output component is initiated in response to a predetermined value detected for a condition.

In one embodiment, the sensor is an orientation sensor, provided to detect an orientation of the device. In a further embodiment, the signal output component is initiated if the detected orientation of the device meets a predetermined orientation. In still a further embodiment, the sensor is a contact sensor provided to detect a contact between the medicament device and the user. In yet a further embodiment, the signal output component is initiated if the detected contact of the device meets a predetermined contact value.

In another embodiment, the sensor is a perpendicularity sensor provided to detect the perpendicularity of the medicament device relative to a surface of the user. In a further embodiment, the signal output component is initiated if the detected perpendicularity of the medicament device meets a predetermined perpendicularity value.

In yet another embodiment, the sensor is provided to detect alignment of the medicament device during operation of the system. In still a further embodiment, the signal output component is initiated if the detected alignment of the medicament device meets a predetermined alignment value. In a further embodiment, an output of the system from the signal output component is initiated in response to a predetermined elapsed time value period occurring within the sequence of instructions. In a further embodiment, the predetermined elapsed time value period comprises a pause between the steps of the instructions. In another embodiment, an output of the device from the signal output component is initiated when the user performs one or more steps in the sequence within a predetermined time period.

In a further embodiment, the system includes a microprocessor. In yet a further embodiment, the system includes a memory module. The memory module may be used to store information about conditions of the device and/or the system, use of the device, information about a particular use, track and record information regarding use of the medicament delivery device or training device. The memory module may be used to track and store information regarding different training or medicament delivery sessions of each user of the system, among other information. Any information tracked or recorded by the system can be transferred to an external location by any method currently known to those of skill in the art. This can be used to ensure compliance with training and/or administering medicament to a user, as the information can be provided to a physician or a family member, in non limiting examples. For example, in an embodiment, the memory module comprises information regarding a condition of the user or the device. The memory module may be removable.

In another embodiment, the signal output comprises an audio output, wherein the audio output can be provided in one or more languages. In a further embodiment, the memory module comprises different languages of a script for guiding the user through the steps of the medicament delivery or medicament delivery simulation/training.

In still a further embodiment, the system includes an indicator that conveys information about a condition of the system. In yet a further embodiment, the indicator may indicate that the medicament delivery and/or training is complete.

In another embodiment, the medicament training system and/or the medicament training container comprises a control interface. In still another embodiment, the medicament training system and/or the medicament training container includes a display to provide information to the user. In still another embodiment, the signal output component generates a visual output including at least one light or screen display, or a combination thereof. In still a further embodiment, the signal output component of the container generates an audio output wherein the audio output comprises a sound or a series of sounds.

In yet another embodiment, the system is connected to an external source, such that information can be communicated to and/or from the system, device and/or the container. In still another embodiment, the information transferred to and/or from the system comprises at least one computer readable file.

In another embodiment, the system further includes a program code module, wherein the program code module records a condition of the device. In a further embodiment, the condition is a user input. In yet a further embodiment, the condition is a status of the system, device and/or the container. In yet a further embodiment, the condition includes an input sensed by the system, device and/or the container. In still another embodiment, the condition includes at least one correct step performed by the user according to the instructions provided by the system.

In another embodiment the condition includes at least one incorrect step performed by the user according to the instructions provided by the system. In a further embodiment, the condition includes usage of the system, device and/or the container. In another embodiment, the condition is an error condition. In a further embodiment, the error condition is a use of the device in an incorrect manner. In another embodiment, the error condition is a failure to complete a step in the use of the device, system and/or the container.

In a further embodiment, the error condition is a failure by the user to use the device to perform one or more steps in the sequence within a predetermined time period. In another embodiment, the medicament device and/or or the system comprises an actuation member, an opening for delivering medicament or simulating medicament delivery to a user, a firing mechanism associated with the actuation member to initiate medicament delivery or simulate medicament delivery. In still a further embodiment, the medicament device includes a medicament delivery simulation mechanism, wherein the medicament delivery simulation mechanism includes a medicament delivery simulation member configured to extend through an opening in the housing of the device when the medicament delivery simulation member is actuated by actuating the actuation member, forcing the member through the opening, such that the medicament delivery simulation member simulates the force and motion of a medicament delivery member without delivering medicament to the user.

In another embodiment, the system is provided wherein the RFID technology includes an RFID transponder and a RFID reader, wherein one of the RFID transponder and the RFID reader is associated with the device and the other is associated with the container. In a further embodiment, the RFID transponder is associated with the device and the RFID reader is associated with the container, wherein the RFID reader of the container powers the device by way of the RFID transponder.

Another embodiment of a medicament training system configured to provide instructions for using a medicament device to a user in a sequence of steps is provided. The system includes a medicament training container, a medicament device, wherein the medicament training container communicatingly connects to the medicament device, a signal output component associated with the medicament training container to provide the sequence of steps and/or feedback to the user, wherein the output from the signal output component is at least one of visual, auditory, tactile, olfactory, or gustatory. The medicament training system further includes circuitry associated with the medicament training container configured so as to control a provision of the instructions to the user in the sequence of steps, one or more sensors associated with the medicament training container and/or the medicament device, a microprocessor associated with the circuitry and the one or more sensors, a memory module configured to store the instructions, and a control interface associated with the medicament training container and/or the medicament device, said control interface comprising one or more responsive members reactive to user input.

In a further embodiment, a medicament training system configured to provide instructions for using the system to a user in a sequence of steps is provided. The medicament training system includes a medicament training container, a medicament device, one or more sensors, a microprocessor, one or more signal output components for providing an output to the user. The medicament training system embodiment includes a storage medium component associated with the microprocessor comprising a database of instructions pertaining to the sequence of steps for using the system stored thereon, one or more program code modules stored on the microprocessor or the storage medium component wherein the one or more program code modules comprise a first program code module for causing the microprocessor to provide a first instruction of the sequence of steps; and a second program code module for causing the microprocessor to provide a subsequent instruction based on a current register.

In a further embodiment, the medicament training system is provided wherein the one or more sensors, the microprocessor and the one or more signal output components are associated with the medicament device and/or the medicament training container. In a further embodiment, the current register includes information about a current step number, a current error condition and/or a current language. In still a further embodiment, the current register comprises information about a current step number and a current error condition. In yet a further embodiment, based on an input received from the one or more sensors, the microprocessor determines whether an error has occurred. In still a further embodiment, when an error has occurred, the microprocessor sets a current error in the current register. In a further embodiment, an attachment device configured to attach to a medicament device is provided. The attachment device includes circuitry to control provision of instructions to a user for using the medicament device in a sequence of steps. In a further embodiment, the attachment device is configured to communicatingly connect to the medicament device. In still a further embodiment, the attachment device includes a control interface In a further embodiment, a medicament training system configured to provide instructions for using a medicament device to a user in a sequence of steps including an attachment device configured to communicatingly connect to a medicament device, and circuitry associated with the attachment device configured so as to control a provision of the instructions to the user in the sequence of steps is provided. In a further embodiment, a signal output component is associated with the attachment device. In still a further embodiment, the attachment device includes at least one sensor. The sensor may be used to detect an orientation, position, location, temperature, airflow, fluid, fluid flow, perpendicularity, contact, and any other feature detectable by a sensor known to those skilled in the art, of the medicament device and/or of the attachment device, in non-limiting embodiments.

In a further embodiment, the attachment device is preprogrammed to interact with various configurations of medicament devices. Medicament devices including inhalation devices, injection devices including autoinjectors, pre-filled syringes or any other devices for parenteral administration of medicament (or related training thereof), devices including medicament bottles or tubes housing medicament (such as, for example, a pill bottle containing capsules or tablets or a vial containing medicament in non-limiting examples). The attachment device can be configured to associate with one or more medicament devices and one or more medicament training containers. Information can be transferred by means known in the art between the medicament device, the attachment device and the medicament training container, such as, for example, compliance information including information about the usage of the system. Additional information may include previous uses of the medicament device, correct and incorrect usage of the system as well as instructions for use of various medicament devices, contraindications related to various medicament devices and various medicaments, possible medicament interactions, safety information and storage information among other information typically associated with medicaments and medicament devices.

In still a further embodiment, the attachment device may be associated with an external device, such as, in a non-limiting example, with a smartphone. Information can be communicated between the attachment device and one or more external devices, or between the medicament training system and one or more external devices. Information can be communicated, as described herein, by way of wired or wireless communication.

In yet a further embodiment, an attachment device configured to attach to a medicament device, wherein the medicament device is configured to deliver medicament to a user is provided. The attachment device includes at least one sensor for sensing operation of the medicament device, and circuitry to provide communication of the operation of the medicament device. The attachment device further includes wherein the circuitry includes a transmitter for wirelessly communicating information about the operation of the medicament device to an external device.

Turning to the drawings, FIG. 1A includes a perspective view of a medicament training system 100 including a medicament training container 20 and a medicament device 10, wherein the medicament training container 20 is configured to house the device 10 within a device cavity 28. The device cavity may include a device removal sensor 25 (which may be a contact sensor, for example). The medicament training container 20 may include a visual display 27 such as an LED backlit image, in a non-limiting embodiment. The container 20 may also include a microphone 26, a speaker 24, and a control interface 19 having, for example, an on/off switch 21, a language selection button 22, and a previous button 23. The container 20 may include a storage cavity 29 configured to receive documentation, instructions for use of the system, etc. The device 10 as shown in the embodiment of the system 100 of FIG. 1A is an auto-injector type medicament device with an actuation button 14; however, the medicament device 10 may also be embodied as an inhaler or respiratory device among other types of medicament delivery and/or training devices.

Figure 1B:
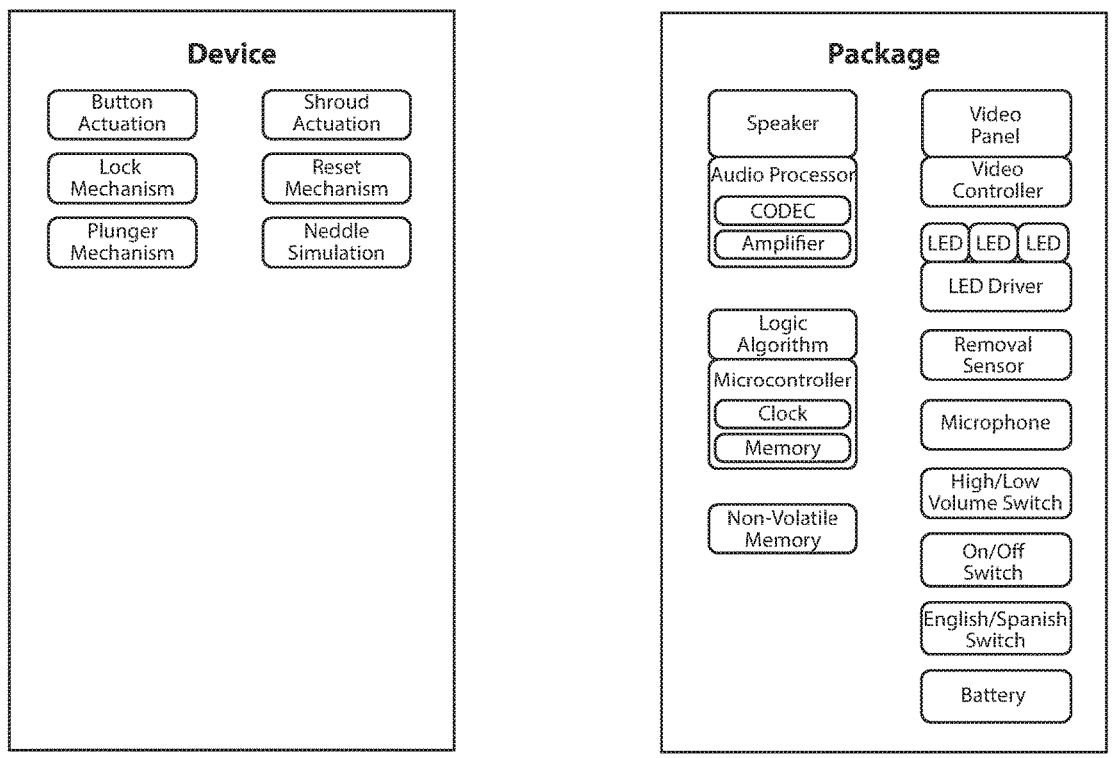
FIG. 1B provides a block diagram of the components of the system of FIG. 1A.

A microcontroller and circuitry may be housed within the container 20 of the system 100. The system may further include a video panel, embedded software with sequential progression through predetermined scripts or segments of training. A piezoelectric dual-tone beeper may be provided as part of the system 100. PCB-mounted membrane switches and high density battery are also options that may be part of this system. The microphone 26 may be used to listen to the device 10 and movements of components of the device 10 which may indicate information about the usage of the device or sounds coming from the device 10 during such usage which may also indicate to a user information about the usage of the device. The microphone 26 may detect clicking sounds from an auto injector medicament delivery device or trainer or a pitch of a whistle sound coming from an inhaler medicament delivery device or trainer which may be indicative of correct or incorrect use of the device 10. The electronics of the system 100 of FIG. 1A may automatically power on once the device 10 is removed from the container 20, in an embodiment. This removal may be detected by the sensor 25. FIG. 1B provides a block diagram demonstrating an example of the separation of components disposed in both the device and the container (i.e., package) of the system 100 of FIG. 1A.

Figure 2A:
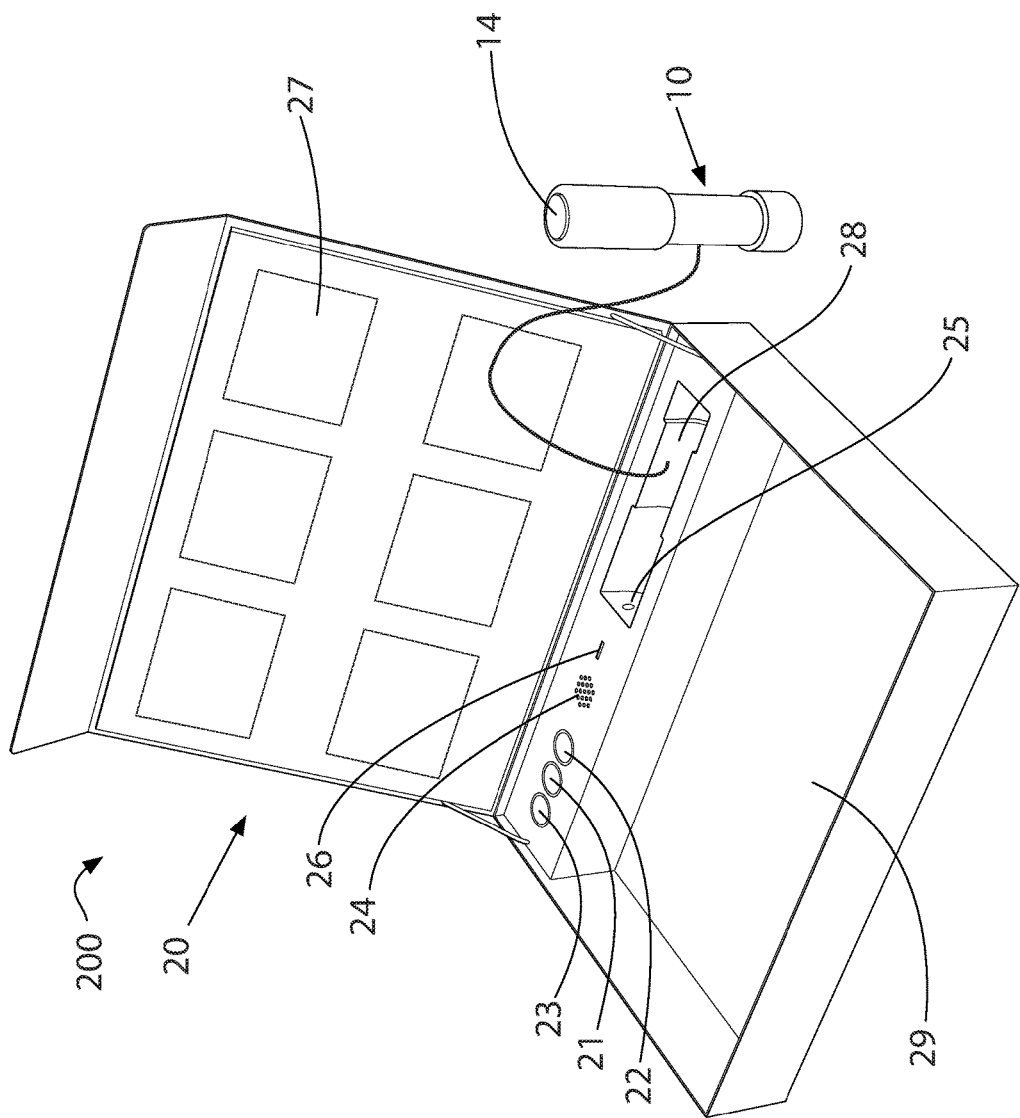
FIG. 2A provides a perspective view of another embodiment of the system.

FIG. 2A provides an embodiment of the medicament training system 200 in which the device 10 is connected to the medicament training container 20 by way of a wire 31. The sensors described within this disclosure can be incorporated into the device 10 and the container 20, therefore allowing for error correction capabilities of the system 200. Error detection and correction as well as error condition notification may be audibly provided to a user, or provided by way of video, tactile output or other such output described herein. Audio error notification can be provided by way of spoken instructions. These may provide encouragement and reinforcement to a user to help prevent errors in the future. For example, when a user error occurs during a step in the sequence, the step will be noted by the system 200 and will be saved in the memory of the system 200, for example, such that when the user reaches that step in a future training or medicament delivery event, the user will be reinforced at that point in the instructions and guided to properly use the system 200 at that step. The instructions may be emphasized at that step, for example, or the user may be required to repeat the step in which the error occurred until it is performed correctly. These are some of the ways in which the system 200 helps the user avoid errors in the future.

Figure 2B:
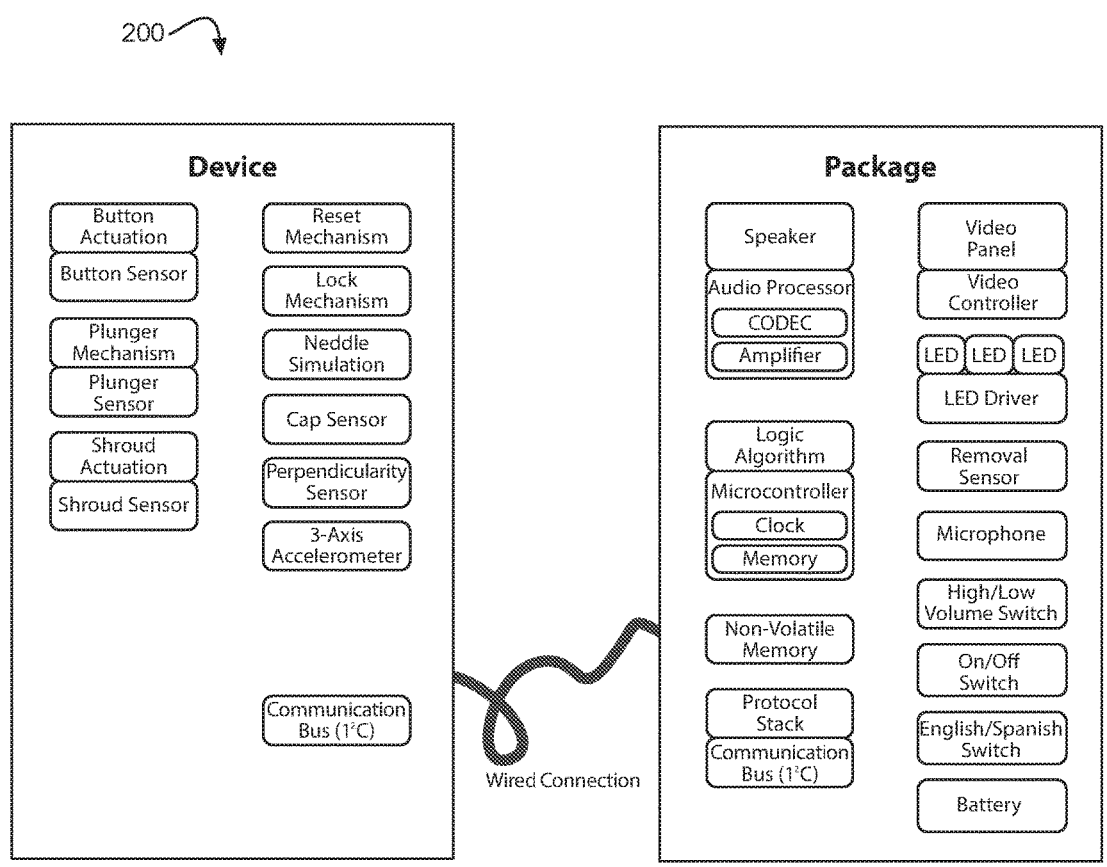
FIG. 2B provides a block diagram of the components of the system of FIG. 2A.

The display 27 of the system 200 may highlight steps in the proper sequence and duration for administration of medicament. The system 200 allows the user to practice synchronization of actions (for example, when using the inhaler, both the compression or activation of the device 10 and the inhalation by the user must be timed properly in order to achieve an optimal result and receive a correct dose of medicament). The system 200 can also measure and indicate timing of the training or medicament delivery event to the user. A dual tone beeper can be provided to help build timing and/or coordination of the user in using the system 200. Embedded software of the system will include error recognition, correction and encouragement algorithms. FIG. 2B provides a block diagram of the separation of components in an example of the system between the device 10 and the container 20.

Figure 3A:
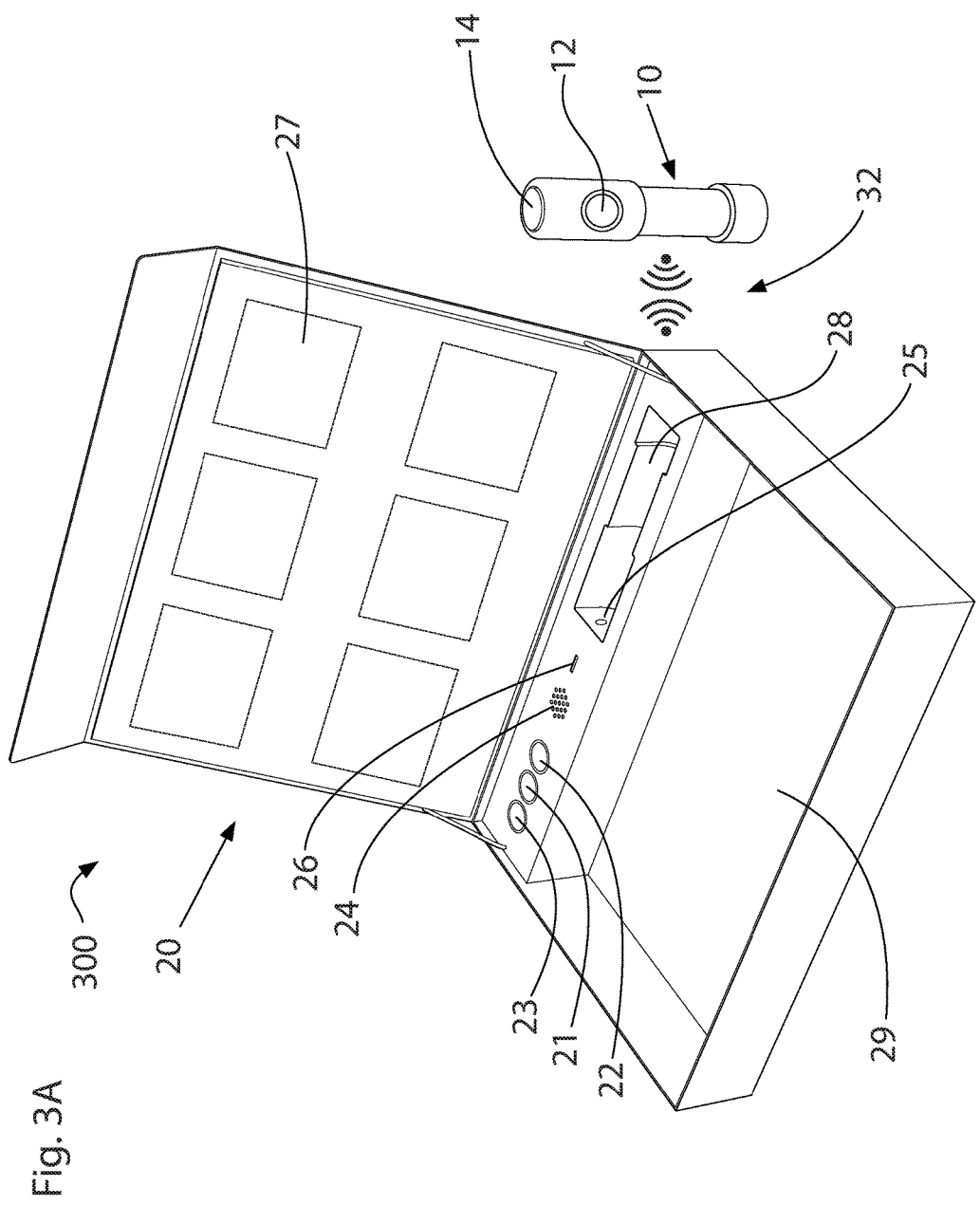
FIG. 3A provides a perspective view of another embodiment of the system.
Figure 3B:
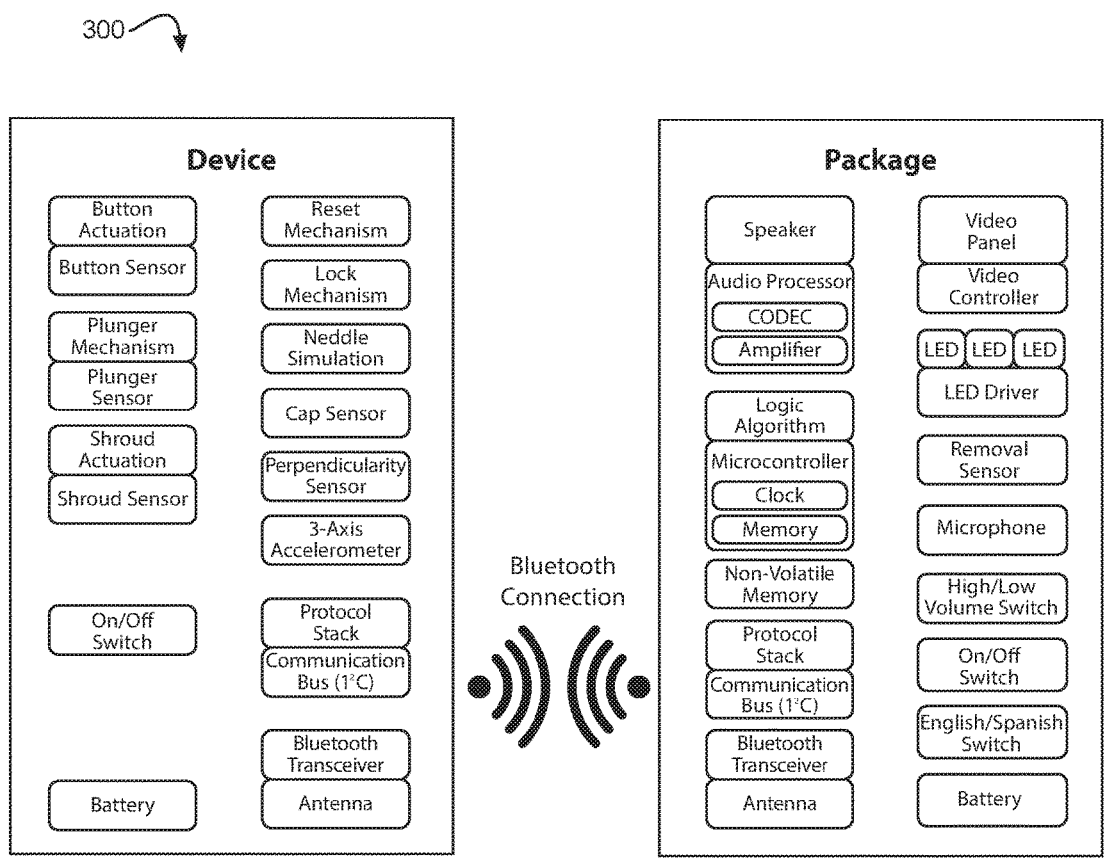
FIG. 3B provides a block diagram of the components of the system of FIG. 3A.

FIG. 3A provides a further embodiment of the medicament training system 300 in which the device 10 and the container 20 are associated by way of wireless connection, (i.e., Bluetooth® connection). In this embodiment, the device 10 will require a battery. The block diagram of FIG. 3B demonstrates an example of the organization of the components of the system 300 between the device 10 and the container 20.

Figure 4A:
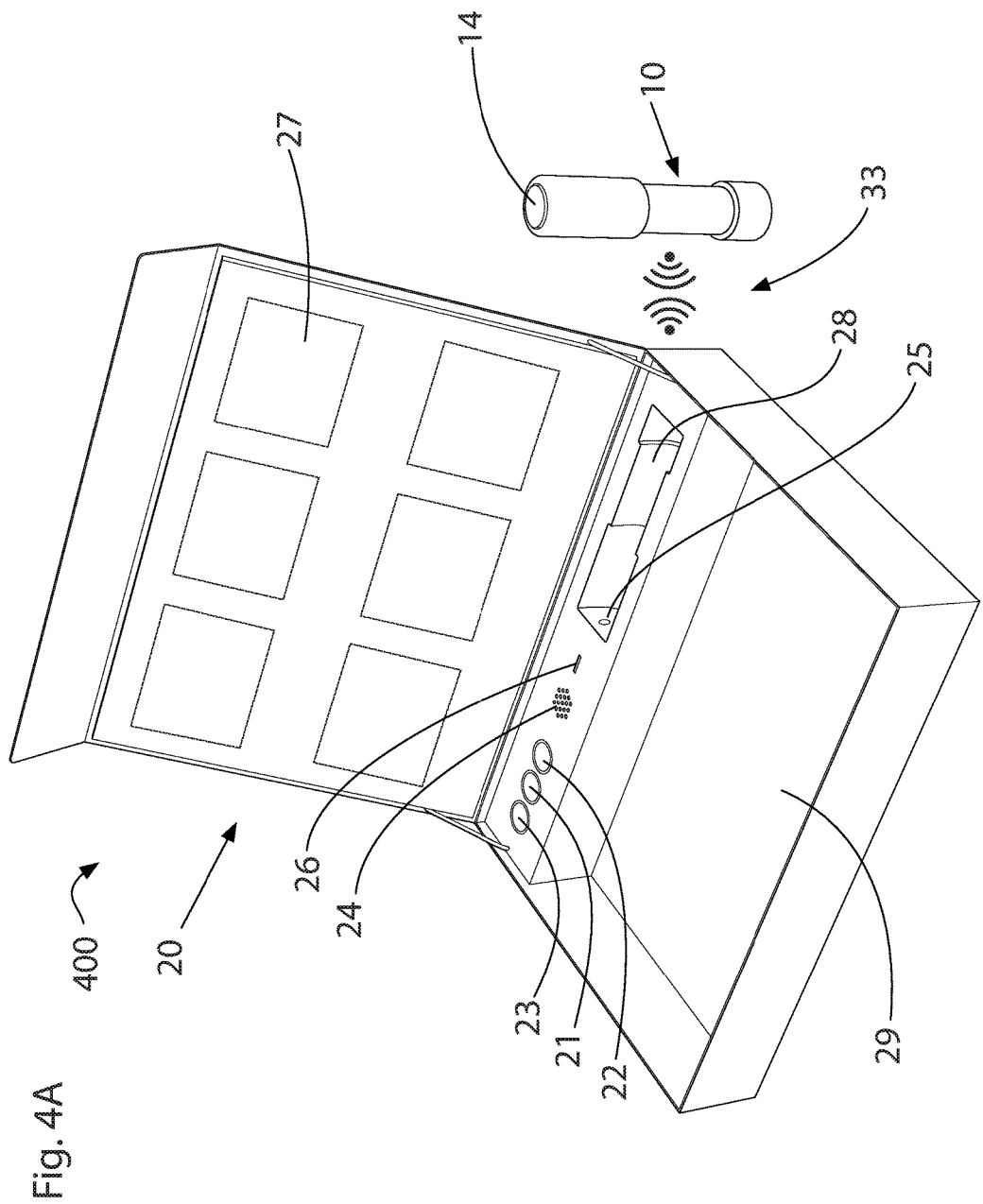
FIG. 4A provides a perspective view of another embodiment of the system.
Figure 4B:
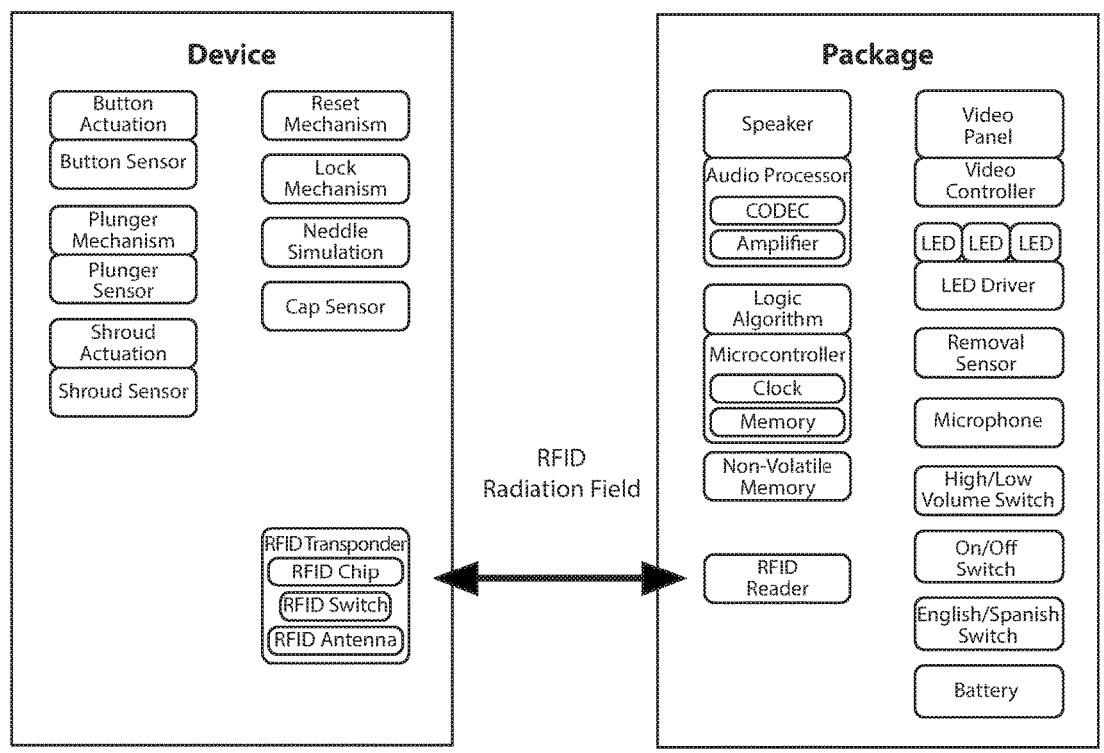
FIG. 4B provides a block diagram of the components of the system of FIG. 4A.

FIG. 4A provides a perspective view of a further embodiment of the medicament training system 400 wherein the device 10 is associated with the container 20 by way of RFID connection 33. FIG. 4B provides block diagram showing a non-limiting example of the organization of the components of the system 400 shown in FIG. 4A as between the device 10 and the container (i.e., package) of the system 400. In the embodiment of the system 400, no battery is required in the device 10 as a result of the RFID technology, wherein the RFID transponder can be disposed in the device 10, which includes the RFID chip, switch and antenna, and the RFID transponder can be powered by the RFID reader in the container (i.e., package) 20. Therefore, by way of the communication between the RFID transponder and reader, no batter is required in the device 10, which allows the size of the device 10 to be advantageously reduced and/or allows for more components of the system 400 to be provided in the device 10 such as sensors, for example.

FIG. 5A provides a front view of an embodiment of the system 500 wherein the container 20 is closed and a device 10 is removed from and disposed in front of the container 20. The medicament delivery and/or training device 10 is embodied as a respiratory inhaler in the embodiment of the system 500 in FIG. 5A. FIG. 5B provides a perspective view of the system 500 wherein the container 20 is in an open position and the respiratory inhaler medicament device 10 has been removed there from. A cavity 28 is provided within a portion of the container 20, wherein the cavity corresponds in shape and size to the medicament device 10. Instructional materials are provided in the inner portion of the container 20. Instructional materials may provide information on usage of the system 500. A control interface 19 for user input and possible output of the system 500 is provided in the inner portion of the container as shown in FIG. 5B.

Figure 6:
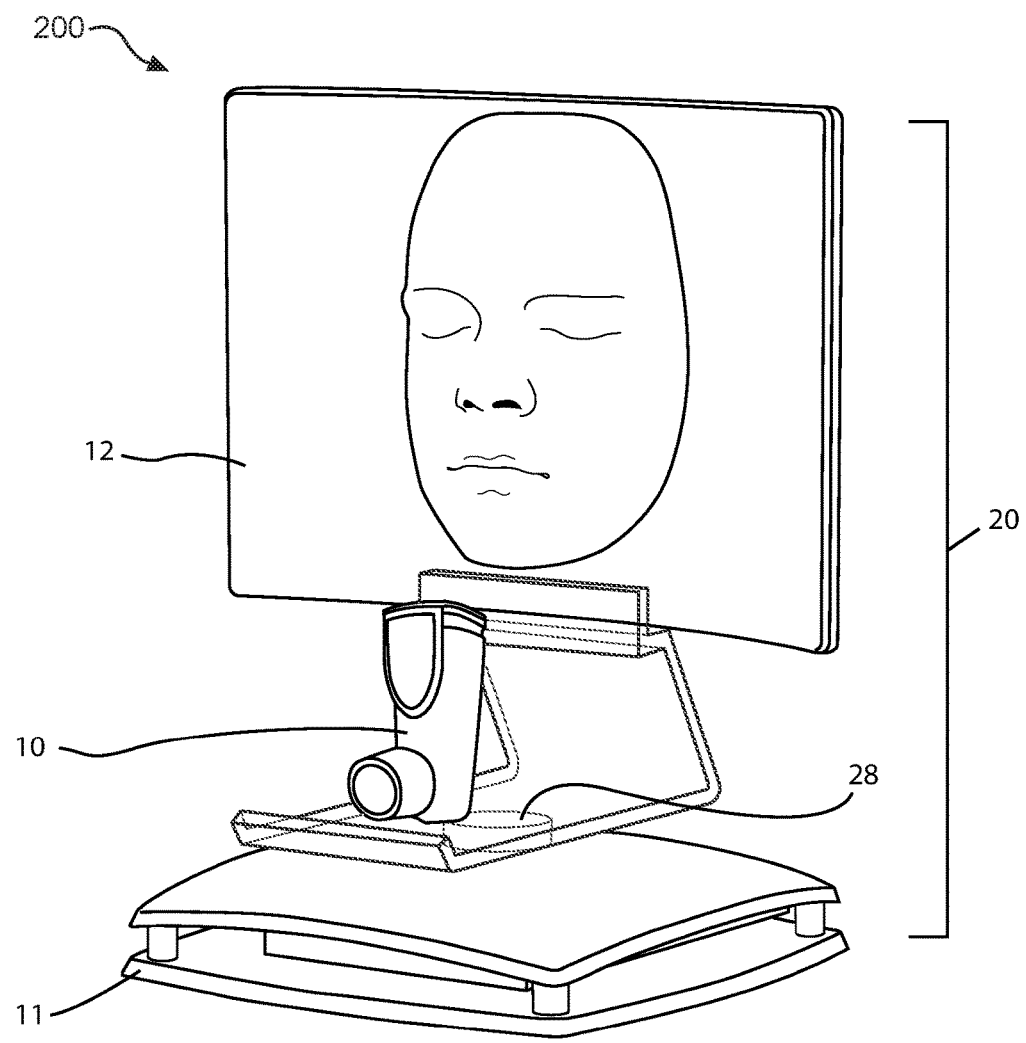
FIG. 6 provides a perspective view of further embodiment of the system.

FIG. 6 provides yet another embodiment of the system 600, wherein the medicament training container 20 is embodied as a display container. The display container 20 includes a cavity for receiving the medicament device 10, a stand 11, and a display board 12 are also provided in the system embodiment 600. The molded face shown on the display board 12 may be used for training with the respiratory inhaler medicament training device 10. The stand 11 may include a drawer for receiving patient brochures and pamphlets. The system 600 may include a display 27 including, in a non-limiting example, an LED display that highlights the sequence and duration of the steps in the medicament administration for training and/or delivery of medicament by a user. The various embodiments of the medicament devices 10 provided herein include both training devices as well as medicament delivery devices.

Figure 7A:
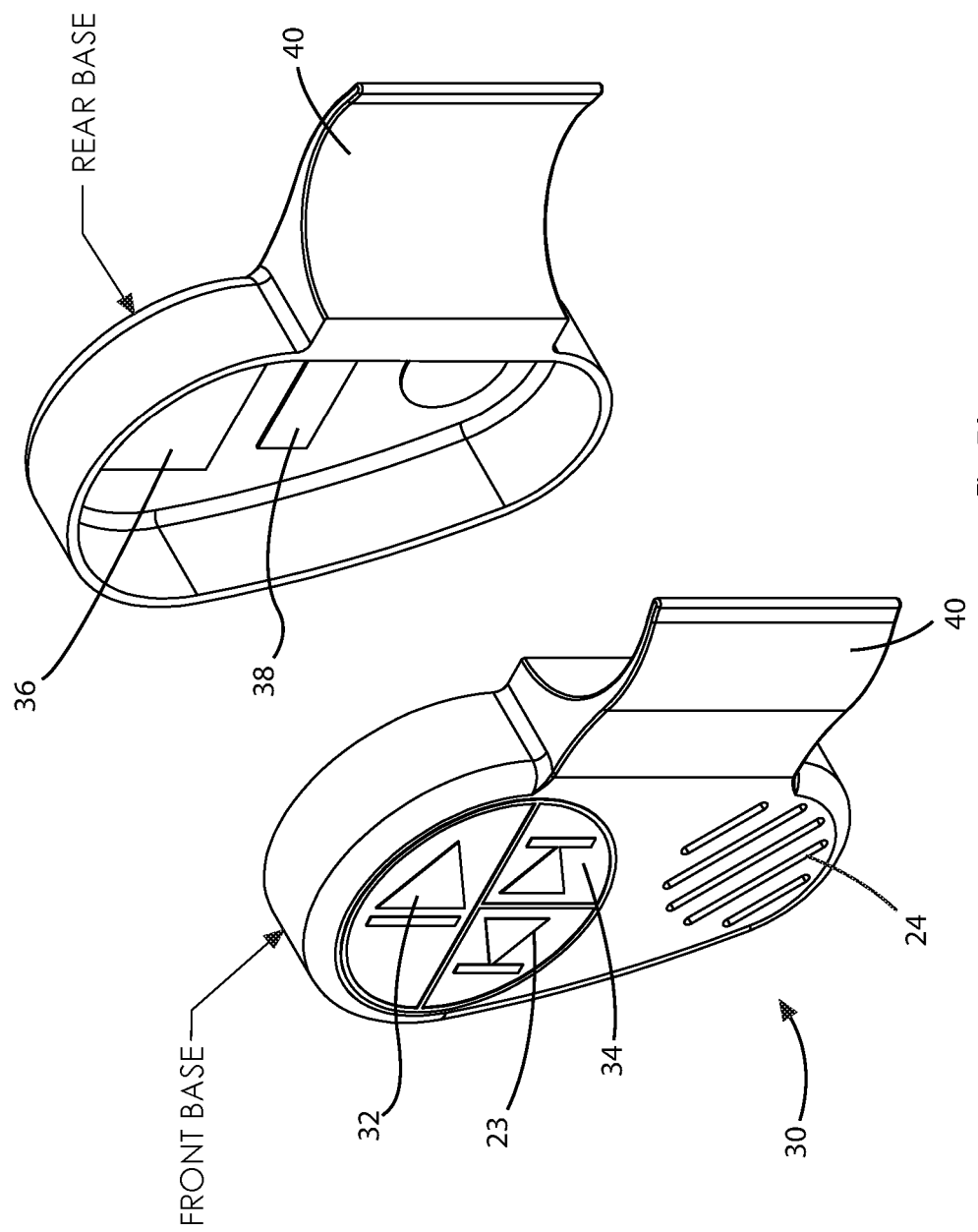
FIG. 7A provides an exploded view of an embodiment of an attachment device.
Figure 7C:
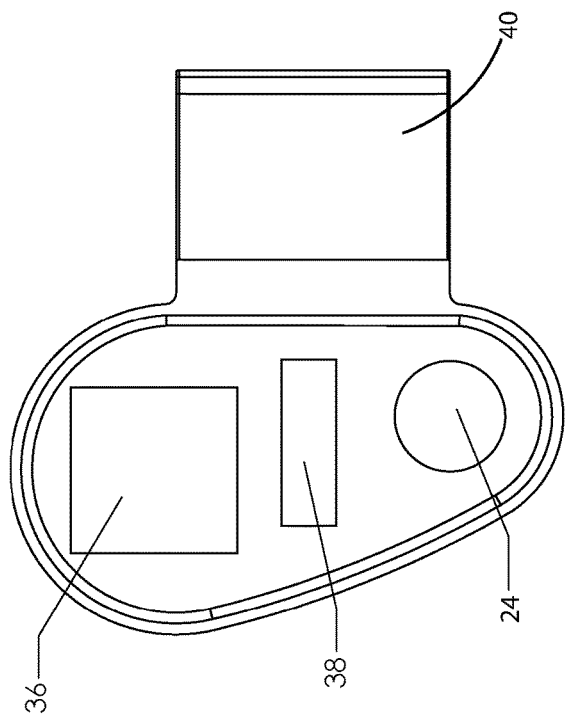
FIG. 7C provides a cross-sectional view of the attachment device of FIG. 7B taken along the x-x axis of FIG. 7B.
Figure 7B:
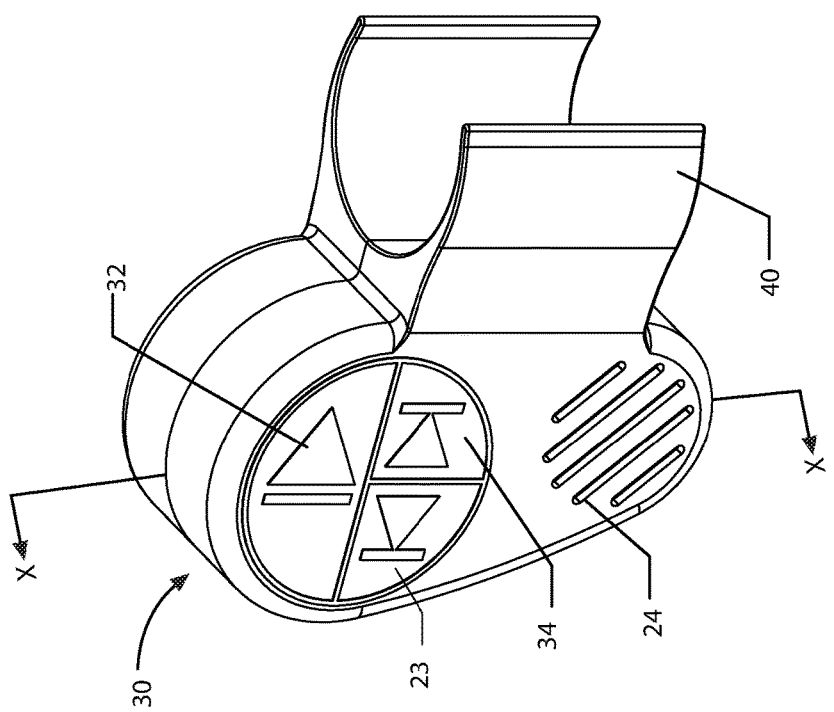
FIG. 7B provides a perspective view of an embodiment of the attachment device of FIG. 7A.

FIGS. 7A-7C provide various views of an embodiment of an attachment device 30. FIG. 7A provides an exploded view of the attachment device 30 embodiment. FIG. 7B provides a perspective view of the attachment device 30 embodiment. FIG. 7C provides a cross-sectional view of the attachment device 30 embodiment, the cross sectional view taken along the x-x axis of the attachment device as seen in FIG. 7B. FIG. 7C shows a schematic illustration of an embodiment of the attachment device 30. In FIGS. 7A and 7C, the circuitry 36 of the attachment device (i.e., PCB), is shown as well as a battery 38 and a speaker 24, in the non-limiting embodiment provided. The attachment device 30 may also include a play button 32, back button 23, and forward button 34 as shown in the embodiment provided. The attachment device 30 may be configured to attach or associate with a medicament device, including but not limited to a housing of a medicament device and/or the medicament device itself. An attachment portion 40 is configured to associate with a medicament device, a medicament training container, or a patient, in non-limiting embodiments. The attachment device 30 can be associated with the medicament device 10 in any way know to those skilled in the art, including but not limited to, by way of direct attachment by clip, Velcro, adhesive, or other direct attachment method, by way of indirect attachment, for example, by wireless connection, such as Bluetooth®, bar code and scanner, radio-frequency communication, among others known to those skilled in the art. The attachment device may further be associated with an external device, such as a Smartphone in one non-limiting embodiment.

The terminology used herein is for the purpose of describing particular embodiments only and is not intended to be limiting. As used herein, the singular forms "a," "an," and "the" are intended to include the plural forms as well, unless the context clearly indicates otherwise these terms do not denote a limitation of quantity, but rather denote the presence of at least one of the referenced item. Furthermore, to the extent that the terms "including," "includes," "having," "has," "with," or variants thereof are used in either the detailed description and/or the claims, such terms are intended to be inclusive in a manner similar to the term "comprising." Moreover, unless specifically stated, any use of the terms first, second, etc., does not denote any order, quantity or importance, but rather the terms first, second, etc., are used to distinguish one element from another.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided. It should be borne in mind that all patents, patent applications, patent publications, technical publications, scientific publications, and other references referenced herein are hereby incorporated by reference in this application in order to more fully describe the state of the art to which the present invention pertains.

While a number of embodiments of the present invention have been shown and described herein in the present context, such embodiments are provided by way of example only, and not of limitation. Numerous variations, changes and substitutions will occur to those of skill in the art without materially departing from the invention herein. For example, the present invention need not be limited to best mode disclosed herein, since other applications can equally benefit from the teachings of the present invention. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

The invention claimed is:

1. A medicament training system configured to provide instructions for using a medicament device to a user in a sequence of steps, comprising:
   a medicament training container;
   a medicament delivery training device comprising a mechanically resettable medicament delivery simulation mechanism comprising a first position when the device is in a pre-delivery state, and a second position when the device is in a post-delivery state, and wherein the mechanism can be reset from the second position to the first position for reuse, wherein said medicament training container communicatively connects to said medicament delivery training device, the medicament delivery training device comprising at least one orientation sensor or at least one contact sensor associated therewith to detect positioning or contact, respectively, of the medicament delivery training device relative to the user during use of the medicament delivery training device;

a signal output component associated with the medicament training container;

a wired or a wireless component, or a combination thereof, for communicatively connecting the medicament training container with the medicament delivery training device; and circuitry associated with the medicament training container configured so as to control a provision of the instructions to the user in the sequence of steps, wherein said circuitry comprises a microprocessor and a memory module;

wherein the medicament training container is programmed to track and store information regarding at least one condition of the user of the medicament delivery training device that occur in different training sessions by a user, wherein the condition comprises at least one incorrect step performed by the user according to the instructions.

2. The system of claim 1, wherein at least a portion of the medicament delivery training device is housed within at least a portion of the medicament training container.

3. The system of claim 2, wherein when the medicament delivery training device is removed from the medicament training container, the provision of instructions is initiated.

4. The system of claim 2, wherein when the medicament delivery training device is removed from the medicament training container, the system is powered on.

5. The system of claim 1, wherein the wireless component comprises a short-range radio frequency technology and/or Radio-Frequency Identification (RFID) technology.

6. The system of claim 1, wherein the medicament delivery training device comprises at least one of a respiratory inhaler trainer and a parenteral drug delivery trainer.

7. The system of claim 1, wherein the medicament delivery training device is a medicament delivery training device configured for medicament delivery to a user.

8. The system of claim 7, wherein the medicament delivery training device comprises at least one of a respiratory inhaler and a parenteral drug delivery device.

9. The system of claim 1, wherein the medicament training container comprises at least one further sensor to detect a condition of the medicament delivery training device.

10. The system of claim 9, wherein an output of the system from the signal output component is initiated in response to a predetermined value detected for a condition.

11. The system of claim 9, wherein the at least one further sensor comprises a perpendicularity sensor provided to detect the perpendicularity of the medicament delivery training device relative to a surface of the user.

12. The system of claim 9, wherein the at least one further sensor is provided to detect alignment of the medicament delivery training device during operation of the system.

13. The system of claim 12, wherein the signal output component is initiated if the detected alignment of the medicament delivery training device meets a predetermined alignment value.

14. The system of claim 1, wherein if the at least one sensor comprises a contact sensor, the signal output component is initiated if the detected contact of the medicament delivery training device meets a predetermined contact value.

15. The system of claim 1, wherein an output of the system from the signal output component is initiated in response to a predetermined elapsed time value period occurring within the sequence of steps.

16. The system of claim 15, wherein the predetermined elapsed time value period comprises a pause between the sequence of steps.

17. The system of claim 1, wherein an output of the device from the signal output component is initiated when the user performs one or more steps in the sequence of steps within a predetermined time period.

18. The system of claim 1, further comprising an indicator that conveys information about a condition of the system, wherein the indicator indicates that the training is complete or incomplete.

19. The system of claim 1, wherein the medicament training container comprises a control interface, a display, or a combination thereof.

20. The system of claim 1, wherein the signal output component generates (i) a visual output comprising at least one light or screen display, or a combination thereof, or (ii) an audio output wherein the audio output comprises a sound or a series of sounds, or a combination of the visual output and the audio output.

21. The system of claim 1, wherein said system is associated with an external source, such that information can be communicated between the external source and the system, the medicament delivery training device, and/or the container.

22. The system of claim 21, wherein the information transferred to the system, medicament delivery training device, or container, from the system, medicament delivery training device or container, or a combination thereof, comprises at least one computer readable file.

23. The system of claim 1, further comprising a program code module, wherein the program code module records a condition of the medicament delivery training device.

24. The system of claim 1 wherein the at least one condition further comprises a status of the device or the container, or a combination thereof; an input sensed by the medicament delivery training device, or the container, or a combination thereof; and at least one correct step performed by the user according to the instructions provided by the system.

25. A medicament training system configured to provide instructions for using a medicament device to a user in a sequence of steps, comprising:

a medicament training container;

a medicament delivery training device comprising at least one orientation sensor or at least one contact sensor associated therewith to detect positioning or contact, respectively, of the medicament delivery training device relative to the user during use of the medicament delivery training device;

a wired component or wireless component to communicatively connect the medicament training container to the medicament delivery training device;

a signal output component associated with the medicament training container;

circuitry associated with the medicament training container comprising a microprocessor and memory module, said circuitry configured so as to control a provision of the instructions to the user in the sequence of steps, wherein the instructions are provided to the user in the sequence of steps and the system provides feedback to the user based on the condition of the medicament delivery training device as detected by the at least one orientation sensor; and wherein the medicament training container is programmed to track and store information regarding at least one condition of the user or the medicament delivery training device that occur in different training sessions by a user, wherein the condition comprises at least one incorrect step performed by the user according to the instructions.

26. The medicament training system of claim 25, wherein an output of the system from the signal output component is initiated in response to a predetermined value detected for the condition.

* * * * *